(12) United States Patent
Chambers et al.

(10) Patent No.: US 7,176,203 B2
(45) Date of Patent: Feb. 13, 2007

(54) IMIDAZO-TRIAZINE DERIVATIVES AS LIGANDS FOR GABA RECEPTORS

(75) Inventors: Mark Stuart Chambers, Puckeridge (GB); Simon Charles Goodacre, Benington (GB); David James Hallett, Watford (GB); Robert James Maxey, Amersham (GB); Michael Geoffrey Neil Russell, Welwyn Garden City (GB); Leslie Joseph Street, Little Hallingbury (GB)

(73) Assignee: Merck Sharp & Dohme Ltd., Hoddesdon ( * ) Notice: Subject to any disclaimer, the term of this patent is extended or adjusted under 35 U.S.C. 154(b) by 116 days.

(21) Appl. No.: 10/512,608

(22) PCT Filed: May 1, 2003

(86) PCT No.: PCT/GB03/01957

§ 371 (c)(1),
(2), (4) Date: Oct. 25, 2004

(87) PCT Pub. No.: WO03/093273

PCT Pub. Date: Nov. 13, 2003

(65) Prior Publication Data

US 2006/0058303 A1    Mar. 16, 2006

(30) Foreign Application Priority Data

May 2, 2002    (GB)    .................. 02101277

(51) Int. Cl.
- C07D 487/04    (2006.01)
- C07D 403/04    (2006.01)
- A61K 31/53    (2006.01)
- A61P 25/22    (2006.01)

(52) U.S. Cl. ...................... 514/243; 544/184

(58) Field of Classification Search ................ 544/184; 514/243
See application file for complete search history.

(56) References Cited

U.S. PATENT DOCUMENTS 3,422,194 A    1/1969    Loev

FOREIGN PATENT DOCUMENTS

| WO | WO 00 12505 | 3/2000 |
| WO | WO 00 23449 | 4/2000 |
| WO | WO 01 14377 | 3/2001 |
| WO | WO 02 38568 | 5/2002 |
| WO | WO 02 076983 | 10/2002 |
| WO | WO 03 008418 | 1/2003 |

OTHER PUBLICATIONS

Scott et al. Prog. Med. Chem. 36: 169-200,1999.*
Saraswathi, T.V. et al: "A one-step synthesis of 3,6-bis-substituted imidazo'1,2-b!-as-triazines, set of highly fluorescrent heterocycles", Indian Journal of Chemistry, Section B: Organic Chemistry Including Medicinal Chemistry, 1977, 15B(7), 607-10.
Povstyanoi, M.V. et al: "Reaction of 3-amino-1,2,4-triazines with alpha. -halo ketones" Ukrainskii Khimicheskii Zhurnal (English Edition) 1976, 42(11), 46-49.
Saldabols, N. et al: "Synthesis inthe methyl 2-furyl ketone series. XII. 5-Nitro-2-furyl substituted imidazo heterocyclic compounds with a common nitrogen atom", Khimiko-Farmatseviticheskii Zhurnal (English Edition) 1967, 2, 83-86.

* cited by examiner

*Primary Examiner*—Venkataraman Balasubramanian
(74) *Attorney, Agent, or Firm*—J. Eric Thies; Melvin Winokur

(57) ABSTRACT

A class of imidazo[1,2*b*][1,2,4]triazine derivatives, substituted at the 7-position by an optionally substituted five-membered or six-membered heteroaromatic ring, being selective ligands for GABA$^A$ receptors, in particular having good affinity for the α2 and/or α3 and/or α5 subunit thereof, are accordingly of benefit in the treatment and/or prevention of adverse conditions of the central nervous system, including anxiety, convulsions and cognitive disorders.

7 Claims, No Drawings

IMIDAZO-TRIAZINE DERIVATIVES AS LIGANDS FOR GABA RECEPTORS

CROSS REFERENCE TO RELATED APPLICATIONS

This application is a U.S. National Phase application under 35 U.S.C. § 371 of PCT Application No. PCT/GB03/01957, filed May. 1, 2003, which claims priority under 35 U.S.C. § 119 from GB Application No. 0210127.7, filed May. 2, 2002.

The present invention relates to a class of substituted imidazo-triazine derivatives and to their use in therapy. More particularly, this invention is concerned with imidazo[1,2-b][1,2,4]triazine analogues which are substituted in the 7-position by an optionally substituted heteroaromatic ring. These compounds are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six α subunits, four β subunits, three γ subunits, one δ subunit, one ε subunit and two ρ subunits.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, δ, ε and ρ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, α1β2γ2, α2βγ1, α2β2/3γ2, α3βγ2/3, α4βδ, α5β3γ2/3, α6βγ2 and α6βδ. Subtype assemblies containing an α1 subunit are present in most areas of the brain and are thought to account for over 40% of $GABA_A$ receptors in the rat. Subtype assemblies containing α2 and α3 subunits respectively are thought to account for about 25% and 17% of $GABA_A$ receptors in the rat. Subtype assemblies containing an α5 subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with a β subunit and γ2. This is the most abundant $GABA_A$ receptor subtype, and is believed to represent almost half of all $GABA_A$ receptors in the brain.

Two other major populations are the α2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2 or α3βγ2 subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which interact more favourably with the α2 and/or α3 subunit than with α1 will be effective in the treatment of anxiety with a reduced propensity to cause sedation. Moreover, agents which are inverse agonists of the α5 subunit are likely to be beneficial in enhancing cognition, for example in subjects suffering from dementing conditions such as Alzheimer's disease. Also, agents which are antagonists or inverse agonists at α1 might be employed to reverse sedation or hypnosis caused by α1 agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; Tourette's syndrome; speech disorders, including stuttering; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse or dependency, including alcohol withdrawal. Selective ligands for GABA$_A$ receptors may be beneficial in enhancing cognition, for example in subjects suffering from dementing conditions such as Alzheimer's disease; and may also be effective as pre-medication prior to anaesthesia or minor procedures such as endoscopy, including gastric endoscopy.

In addition, the compounds in accordance with the present invention may be useful as radioligands in assays for detecting compounds capable of binding to the human GABA$_A$ receptor.

The present invention provides a class of imidazo-triazine derivatives which possess desirable binding properties at various GABA$_A$ receptor subtypes. The compounds in accordance with the present invention have good affinity as ligands for the α2 and/or α3 and/or α5 subunit of the human GABA$_A$ receptor. The compounds of this invention may interact more favourably with the α2 and/or α3 subunit than with the α1 subunit; and/or may interact more favourably with the α5 subunit than with the α1 subunit.

The compounds of the present invention are GABA$_A$ receptor subtype ligands having a binding affinity ($K_i$) for the α2 and/or α3 and/or α5 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 and/or α5 subunit relative to the α1 subunit. However, compounds which are not selective in terms of their binding affinity for the α2 and/or α3 and/or α5 subunit relative to the α1 subunit are also encompassed within the scope of the present invention; such compounds will desirably exhibit functional selectivity in terms of zero or weak (positive or negative) efficacy at the α1 subunit and (i) a full or partial agonist profile at the α2 and/or α3 subunit, and/or (ii) an inverse agonist profile at the α5 subunit.

The present invention provides a compound of formula I, or a salt or prodrug thereof:

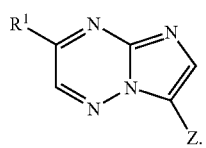

(I)

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole; or Z represents an optionally substituted six-membered heteroaromatic ring selected from pyridine, pyrazine, pyrimidine and pyridazine;

R$^1$ represents hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$ or —CR$^a$=NOR$^b$; and R$^a$ and R$^b$ independently represent hydrogen, hydrocarbon or a heterocyclic group.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z.

Where Z in the compounds of formula I above represents a six-membered heteroaromatic ring, this ring may be optionally substituted by one or more substituents, typically by one or two substituents.

Suitably, the group Z is unsubstituted or monosubstituted.

Examples of optional substituents on the five-membered or six-membered heteroaromatic ring as specified for Z include halogen, cyano, trifluoromethyl, C$_{1-6}$ alkyl, halo(C$_{1-6}$)alkyl, dihalo(C$_{1-6}$)alkyl, hydroxy(C$_{1-6}$)alkyl, C$_{1-6}$ alkoxy(C$_{1-16}$)alkyl, C$_{3-7}$ cycloalkyl, C$_{3-7}$ heterocycloalkyl, benzyl-tetrahydropyridinyl, oxy, hydroxy, C$_{1-6}$ alkoxy, methyltriazolyl(C$_{1-6}$)alkoxy, C$_{1-6}$ alkylthio, C$_{1-6}$ alkylsulphonyl, C$_{2-6}$ alkylcarbonyl, amino, C$_{1-6}$ alkylamino, di(C$_{1-6}$) alkylamino, C$_{2-6}$ alkylcarbonylamino, phenyl, (C$_{1-6}$)alkylphenyl, halophenyl, dihalophenyl, trihalophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (halo)(trifluoromethyl)phenyl, nitrophenyl, methoxyphenyl, (halo)(methoxy)phenyl, trifluoromethoxy-phenyl, (halo)(trifluoromethoxy)phenyl, methylenedioxy-phenyl, (C$_{2-6}$)alkylcarbonyl-phenyl, trifluorothio-phenyl, (C$_{1-6}$)alkylsulphonyl-phenyl, di(C$_{1-6}$)alkylaminocarbonyl-phenyl, di(C$_{1-6}$) alkylaminosulphonyl-phenyl, (halo)(morpholinylmethyl) phenyl, (halo)(pyridinyl)phenyl, imidazolyl-phenyl, thiadiazolyl-phenyl, methylthiadiazolyl-phenyl, (halo)(triazolyl)phenyl, methyltetrazolyl-phenyl and optionally substituted heteroaryl, the optional substituents on the heteroaryl moiety being typically selected from oxy, halogen, cyano and C$_{1-6}$ alkyl.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$)alkyl, indanyl, aryl and aryl(C$_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include C$_{3-7}$ heterocycloalkyl, C$_{3-7}$ heterocycloalkyl(C$_{1-6}$)alkyl, heteroaryl and heteroaryl(C$_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "$C_{1-6}$ alkoxy", "$C_{1-6}$ alkylamino" and "$C_{1-6}$ alkylsulphonyl" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of $C_{3-7}$ cycloalkyl($C_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl, preferably phenyl.

Particular aryl($C_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-16}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR'R$^w$, —NR$^v$COR$^w$, —NR$^v$CO$_2$R$^w$, —NR$^v$SO$_2$R$^w$, —CH$_2$NR$^v$SO$_2$R$^w$, —NHCONR'R$^w$, —CONR'R$^w$, —SO$_2$NR'R$^w$ and —CH$_2$SO$_2$NR'R$^w$, in which R$^v$ and R$^w$ independently represent hydrogen, $C_{1-6}$ alkyl, aryl or aryl($C_{1-6}$)alkyl.

The term "halogen" as used herein includes fluorine, chlorine, bromine and iodine, especially fluoro or chloro.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

The present invention includes within its scope tautomers of the compounds of formula I as defined above. For example, where Z represents an optionally substituted 2-hydroxypyridine moiety, this may co-exist, in whole or in part, with the corresponding 2-pyridone tautomer. It is to be understood that all such tautomers and mixtures thereof in any proportion are encompassed within the scope of the present invention.

Where the group Z represents an optionally substituted five-membered heteroaromatic ring, this is suitably a thiophene, thiazole or thiadiazole ring, either of which may be optionally substituted by one or, where possible, two substituents.

Where the group Z represents an optionally substituted six-membered heteroaromatic ring, this is suitably a pyridinyl or pyrimidinyl ring, either of which may be optionally substituted by one or more substituents, typically by one or two substituents. In one embodiment, Z represents monosubstituted pyridinyl. In another embodiment, Z represents monosubstituted pyrimidinyl.

Illustrative examples of optional substituents on the group Z include fluoro, chloro, bromo, iodo, cyano, trifluoromethyl, methyl, isopropyl, tert-butyl, chloromethyl, fluoropropyl (especially 2-fluoroprop-2-yl), difluoroethyl (especially 1,1-difluoroethyl), hydroxypropyl (especially 2-hydroxyprop-2-yl), methoxymethyl, cyclopentyl, pyrrolidinyl, morpholinyl, benzyl-tetrahydropyridinyl, oxy, hydroxy, methoxy, ethoxy, isopropoxy, tert-butoxy, methyltriazolyl-methoxy, methylthio, ethylthio, methanesulphonyl, acetyl, tert-butylamino, dimethylamino, acetylamino, phenyl, methylphenyl, isopropylphenyl, tert-butylphenyl, fluorophenyl, chlorophenyl, bromophenyl, difluorophenyl, dichlorophenyl, dibromophenyl, (chloro)(fluoro)phenyl, trifluorophenyl, trichlorophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (chloro)(trifluoromethyl)phenyl, nitrophenyl, methoxyphenyl, (fluoro)(methoxy)phenyl, trifluoromethoxy-phenyl, (fluoro)(trifluoromethoxy)phenyl, methylenedioxy-phenyl, acetylphenyl, trifluorothio-phenyl, methanesulphonyl-phenyl, ethanesulphonyl-phenyl, dimethylaminocarbonyl-phenyl, dimethylaminosulphonyl-phenyl, (fluoro)(morpholinylmethyl)phenyl, (fluoro)(pyridinyl)phenyl, imidazolyl-phenyl, thiadiazolyl-phenyl, methylthiadiazolyl-phenyl, (fluoro)(triazolyl)phenyl, methyltetrazolyl-phenyl, pyridinyl, oxypyridinyl, fluoropyridinyl, chloropyridinyl, cyanopyridinyl, methylpyridinyl, dimethyl-pyridinyl, pyridazinyl, pyrimidinyl, pyrazinyl, furyl, thienyl, cyanothienyl, pyrrolyl, pyrazolyl, oxazolyl, thiazolyl, isothiazolyl, imidazolyl, methylimidazolyl and triazolyl.

Typical examples of optional substituents on the group Z include chloro, oxy, hydroxy, cyanophenyl, (cyano)(fluoro)phenyl, pyridinyl and cyanopyridinyl.

One particular substituent on the group Z is cyanophenyl, especially 2-cyanophenyl.

Another particular substituent on the group Z is (cyano)(fluoro)phenyl, especially 2-cyano-4-fluorophenyl.

A further particular substituent on the group Z is pyridinyl, especially pyridin-4-yl.

An additional particular substituent on the group Z is cyanopyridinyl, especially 3-cyanopyridin-2-yl.

Typically, $R^1$ represents hydrogen, hydrocarbon, a heterocyclic group, halogen, cyano, trifluoromethyl, —$OR^a$, —$COR^a$, —$CO_2R^a$ or —$CR^a$=$NOR^b$.

Typical values of $R^a$ include hydrogen and $C_{1-6}$ alkyl. Suitably, $R^a$ represents hydrogen or methyl.

Typical values of $R^b$ include hydrogen, $C_{1-6}$ alkyl, hydroxy($C_{1-6}$)alkyl and di($C_{1-6}$)alkylamino($C_{1-6}$)alkyl. Suitably, $R^b$ represents hydrogen, methyl, ethyl, hydroxyethyl or dimethylaminoethyl. Particular values of $R^b$ include hydrogen, hydroxyethyl and dimethylaminoethyl, especially hydrogen or dimethylaminoethyl.

Representative values of $R^1$ include hydrogen, $C_{1-6}$ alkyl, halo($C_{1-6}$)alkyl, dihalo($C_{1-6}$)alkyl, hydroxy($C_{1-6}$)alkyl, $C_{1-6}$ alkoxy($C_{1-6}$)alkyl, di($C_{1-6}$)alkoxy($C_{1-6}$)alkyl, cyano($C_{1-6}$)alkyl, $C_{3-7}$ cycloalkyl, heteroaryl, $C_{1-6}$ alkyl-heteroaryl, heteroaryl($C_{1-6}$)alkyl, halogen, cyano, trifluoromethyl, $C_{1-6}$ alkoxy, formyl, $C_{2-6}$ alkylcarbonyl, $C_{2-6}$ alkoxycarbonyl and —$CR^a$=$NOR^b$, in which $R^a$ and $R^b$ are as defined above.

Itemised values of $R^1$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), fluoropropyl (especially 2-fluoroprop-2-yl), cyanopropyl (especially 2-cyanoprop-2-yl), tert-butyl, cyclopropyl, cyclobutyl, pyridinyl, furyl, thienyl, oxazolyl, methylthiazolyl, methyloxadiazolyl, imidazolylmethyl, triazolylmethyl, chloro, cyano, trifluoromethyl, methoxy, formyl, acetyl, methoxycarbonyl and —$CR^2$=$NOR^3$, in which $R^2$ represents hydrogen or methyl, and $R^3$ represents hydrogen, hydroxyethyl or dimethylaminoethyl.

Individual values of $R^1$ include dimethoxyethyl (especially 1,1-dimethoxyethyl), cyanopropyl (especially 2-cyanoprop-2-yl), hydroxypropyl (especially 2-hydroxyprop-2-yl), fluoropropyl (especially 2-fluoroprop-2-yl), tert-butyl, triazolylmethyl, trifluoromethyl and acetyl.

A favoured value of $R^1$ is 2-hydroxyprop-2-yl.

A particular value of $R^1$ is trifluoromethyl.

Suitably, $R^2$ is hydrogen.

Suitably, $R^3$ represents hydrogen or dimethylaminoethyl, especially hydrogen.

A particular sub-class of compounds according to the invention is represented by the compounds of formula IA, and salts and prodrugs thereof:

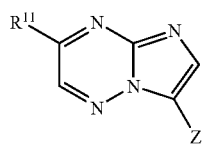

(IA)

wherein

Z is as defined above;

$R^{11}$ represents hydrogen, $C_{1-6}$ alkyl, cyano($C_{1-6}$)alkyl, halo($C_{1-6}$)allyl, dihalo($C_{1-6}$)alkyl, hydroxy($C_{1-6}$)alkyl, $C_{1-6}$ alkoxy($C_{1-6}$)alkyl, di($C_{1-6}$)alkoxy($C_{1-6}$)alkyl, $C_{3-7}$ cycloalkyl, heteroaryl, $C_{1-6}$ alkyl-heteroaryl, heteroaryl($C_{1-6}$)alkyl, halogen, cyano, trifluoromethyl, $C_{1-6}$ alkoxy, formyl, $C_{2-6}$ alkylcarbonyl, $C_{2-6}$ alkoxycarbonyl or —$CR^4$=$NOR^5$;

$R^4$ represents hydrogen or $C_{1-6}$ alkyl; and $R^5$ represents hydrogen, $C_{1-6}$ alkyl, hydroxy($C_{1-6}$)alkyl or di($CO_{1-6}$)alkylamino($C_{1-6}$)alkyl.

Suitably, $R^4$ represents hydrogen or methyl, especially hydrogen.

Suitably, $R^5$ represents hydrogen, methyl, ethyl, hydroxyethyl or dimethylaminoethyl. Particular values of $R^5$ include hydrogen, hydroxyethyl and dimethylaminoethyl. Typically, $R^5$ represents hydrogen or dimethylaminoethyl, especially hydrogen.

Where $R^{11}$ represents heteroaryl, this group is suitably pyridinyl, furyl, thienyl or oxazolyl.

Where $R^{11}$ represents $C_{1-6}$ alkyl-heteroaryl, this group is suitably methylthiazolyl (e.g. 2-methylthiazol-5-yl) or methyloxadiazolyl (e.g. 3-methyl-[1,2,4]oxadiazol-5-yl).

Where $R^{11}$ represents heteroaryl($C_{1-6}$)alkyl, this group is suitably imidazolylmethyl or triazolylmethyl.

Itemised values of $R^{11}$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), fluoropropyl (especially 2-fluoroprop-2-yl), cyanopropyl (especially 2-cyanoprop-2-yl), tert-butyl, cyclopropyl, cyclobutyl, pyridinyl, furyl, thienyl, oxazolyl, methylthiazolyl, methyloxadiazolyl, imidazolylmethyl, triazolylmethyl, chloro, cyano, trifluoromethyl, methoxy, formyl, acetyl, methoxycarbonyl and —$CR^2$=$NOR^3$, in which $R^2$ and $R^3$ are as defined above.

Representative values of $R^{11}$ include dimethoxyethyl (especially 1,1-dimethoxyethyl), cyanopropyl (especially 2-cyanoprop-2-yl), hydroxypropyl (especially 2-hydroxyprop-2-yl), fluoropropyl (especially 2-fluoroprop-2-yl), tert-butyl, triazolylmethyl, trifluoromethyl and acetyl.

A favoured value of $R^{11}$ is 2-hydroxyprop-2-yl.

A particular value of $R^{11}$ is trifluoromethyl.

One representative subset of the compounds of formula IA above is represented by the compounds of formula IIA, and salts and prodrugs thereof:

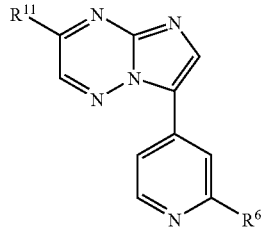

(IIA)

wherein $R^6$ represents hydrogen, halogen, cyano, trifluoromethyl, $C_{1-6}$ alkyl, halo($C_{1-6}$)alkyl, dihalo($C_{1-6}$)alkyl, hydroxy($C_{1-6}$) alkyl, $C_{1-6}$ alkoxy($C_{1-6}$)alkyl, $C_{3-7}$ cycloalkyl, $C_{3-7}$ heterocycloalkyl, benzyl-tetrahydropyridinyl, $C_{1-6}$ alkoxy, methyltriazolyl($C_{1-6}$)alkoxy, $C_{1-6}$ alkylthio, $C_{1-6}$ alkylsulphonyl, $C_{2-6}$ alkylcarbonyl, amino, $C_{1-6}$ alkylamino, di($C_{1-6}$)alkylamino, $C_{2-6}$ alkylcarbonylamino, phenyl, ($C_{1-6}$)alkyl-phenyl, halophenyl, dihalophenyl, trihalophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (halo)(trifluoromethyl)phenyl, nitrophenyl, methoxyphenyl, (halo)(methoxy)phenyl, trifluoromethoxy-phenyl, (halo)(trifluoromethoxy)phenyl, methylenedioxy-phenyl, ($C_{2-6}$)alkylcarbonyl-phenyl, trifluorothio-phenyl, ($C_{1-6}$)alkylsulphonyl-phenyl, di($C_{1-6}$)alkylaminocarbonyl-phenyl, di($C_{1-6}$)alkylaminosulphonyl-phenyl, (halo)(morpholinylmethyl)phenyl, (halo)(pyridinyl)phenyl, imidazolyl-phenyl, thiadiazolyl-phenyl, methylthiadiazolyl-phenyl, (halo)(triazolyl)phenyl, methyltetrazolyl-phenyl or optionally substituted heteroaryl, the optional substituents on the heteroaryl moiety being selected from oxy, halogen, cyano and $C_{1-6}$ alkyl; and $R^{11}$ is as defined above.

Illustrative values of $R^6$ include hydrogen, fluoro, chloro, bromo, iodo, cyano, trifluoromethyl, methyl, isopropyl, tert-butyl, chloromethyl, fluoropropyl (especially 2-fluoroprop-2-yl), difluoroethyl (especially 1,1-difluoroethyl), hydroxypropyl (especially 2-hydroxyprop-2-yl), methoxymethyl, cyclopentyl, pyrrolidinyl, morpholinyl, benzyl-tetrahydropyridinyl, methoxy, ethoxy, isopropoxy, tert-butoxy, methyltriazolyl-methoxy, methylthio, ethylthio, methanesulphonyl, acetyl, tert-butylamino, dimethylamino, acetylamino, phenyl, methylphenyl, isopropylphenyl, tert-butylphenyl, fluorophenyl, chlorophenyl bromophenyl, difluorophenyl, dichlorophenyl, dibromophenyl, (chloro)(fluoro)phenyl, trifluorophenyl, trichlorophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (chloro)(trifluoromethyl)phenyl, nitrophenyl, methoxyphenyl, (fluoro)(methoxy)phenyl, trifluoromethoxy-phenyl, (fluoro)(trifluoromethoxy)phenyl, methylenedioxy-phenyl, acetylphenyl, trifluorothio-phenyl, methanesulphonyl-phenyl, ethanesulphonyl-phenyl, dimethylaminocarbonyl-phenyl, dimethylaminosulphonyl-phenyl, (fluoro)(morpholinylmethyl)phenyl, (fluoro)(pyridinyl)phenyl, imidazolyl-phenyl, thiadiazolyl-phenyl, methylthiadiazolyl-phenyl, (fluoro)(triazolyl)phenyl, methyltetrazolyl-phenyl, pyridinyl, oxypyridinyl, fluoropyridinyl, chloropyridinyl, cyanopyridinyl, methylpyridinyl, dimethyl-pyridinyl, pyridazinyl, pyrimidinyl, pyrazinyl, furyl, thienyl, cyanothienyl, pyrrolyl, pyrazolyl, oxazolyl, thiazolyl, isothiazolyl, imidazolyl, methylimidazolyl and triazolyl.

In one embodiment, $R^6$ represents cyanophenyl, especially 2-cyanophenyl.

In another embodiment, $R^6$ represents (cyano)(fluoro)phenyl, especially 2-cyano-4-fluorophenyl.

In a further embodiment, $R^6$ represents pyridinyl, especially pyridin-4-yl.

In an additional embodiment, $R^6$ represents cyanopyridinyl, especially 3-cyanopyridin-2-yl.

An illustrative subset of the compounds of formula IIA above is represented by the compounds of formula IIB, and salts and prodrugs thereof:

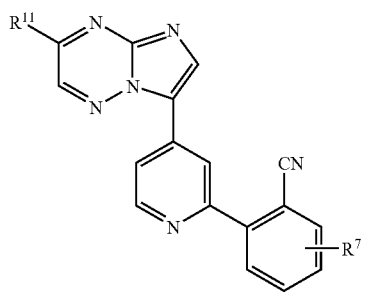

(IIB)

wherein $R^{11}$ is as defined above; and $R^7$ represents hydrogen or fluoro.

In one embodiment, $R^7$ is hydrogen.

In another embodiment, $R^7$ is fluoro, in which case the fluorine atom $R^7$ is favourably attached to the phenyl ring at the 4-, 5- or 6-position (relative to the cyano group at position 2), preferably at the 4-position.

Another representative subset of the compounds of formula IA above is represented by the compounds of formula IIC, and salts and prodrugs thereof.

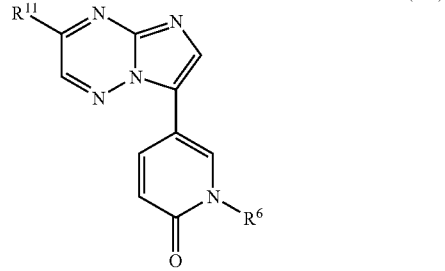

(IIC)

wherein $R^6$ and $R^{11}$ are as defined above.

Specific compounds within the scope of the present invention include:

2-[4-(3-trifluoromethylimidazo[1,2-b][1,2,4]triazin-7-yl)pyridin-2-yl]-benzonitrile;

5-fluoro-2-[4-(3-trifluoromethylimidazo[1,2-b][1,2,4]triazin-7-yl)pyridin-2-yl]benzonitrile;

4-(3-trifluoromethylimidazo[1,2-b][1,2,4]triazin-7-yl)-[2,4']bipyridinyl;

5-[3-(1-hydroxy-1-methylethyl)imidazo[1,2-b][1,2,4]triazin-7-yl]-2-oxo-2H-[1,2']bipyridinyl-3'-carbonitrile;

and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the anxiolytic compounds of the invention is ideally 50 nM or less, preferably 10 nM or less, and more preferably 5 nM or less.

The anxiolytic compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA EC20 response in stably transfected cell lines expressing the α3 and α1 subunits of the human GABA$_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention may exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are likely to be substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In another aspect, the present invention provides a method for the treatment and/or prevention of cognitive disorders, including dementing conditions such as Alzheimer's disease, which comprises administering to a patient in need of such treatment an effective amount of a compound of formula I as defined above or a pharmaceutically acceptable salt thereof.

Cognition enhancement can be shown by testing the compounds in the Morris watermaze as reported by McNamara and Skelton, *Psychobiology*, 1993, 21, 101–108. Further details of relevant methodology are described in WO 96/25948.

Cognitive disorders for which the compounds of the present invention may be of benefit include delirium, dementia, amnestic disorders, and cognition deficits, including age-related memory deficits, due to traumatic injury, stroke, Parkinson's disease and Down Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV disease, head trauma, Parkinson's disease or Creutzfeld-Jakob disease.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of neurological disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

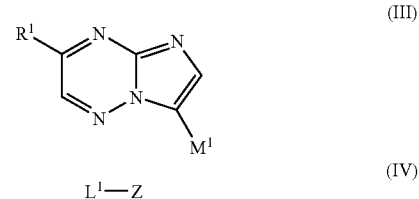

wherein Z and R$^1$ are as defined above, L$^1$ represents a suitable leaving group, and M$^1$ represents a boronic acid moiety —B(OH)$_2$ or a cyclic ester thereof formed with an organic diol, e.g. pinacol, 1,3-propanediol or neopentyl glycol, or M$^1$ represents —Sn(Alk)$_3$ in which Alk represents a C$_{1-6}$ alkyl group, typically n-butyl; in the presence of a transition metal catalyst.

The leaving group L$^1$ is typically a halogen atom, e.g. bromo or chloro.

The transition metal catalyst of use in the reaction between compounds III and IV is suitably tetrakis(triphenylphosphine)-palladium(0). The reaction is conveniently carried out at an elevated temperature in a solvent such as tetrahydrofuran, 1,4-dioxane or N,N-dimethylacetamide, typically in the presence of potassium phosphate, sodium carbonate, cesium carbonate or copper(I) iodide.

In an alternative procedure, the compounds according to the present invention may be prepared by a process which comprises reacting a compound of formula V with a compound of formula VI:

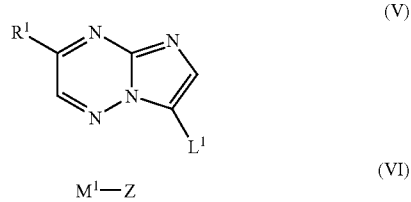

(V)

(VI)

wherein Z, $R^1$, $L^1$ and $M^1$ are as defined above; in the presence of a transition metal catalyst; under conditions analogous to those described above for the reaction between compounds III and IV.

In another procedure, the compounds according to the present invention wherein Z represents a thiazol-2-yl moiety substituted at the 4-position by a substituent $R^8$, in which $R^8$ represents any allowable substituent on the group Z (in particular wherein $R^8$ represents pyridin-3-yl), may be prepared by a process which comprises reacting a compound of formula VII with a compound of formula VIII:

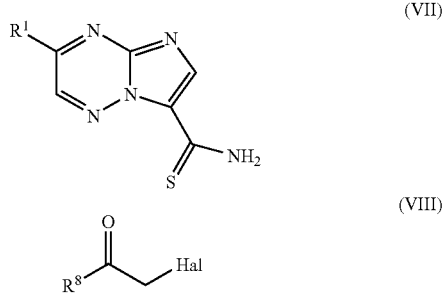

(VII)

(VIII)

wherein $R^1$ and $R^8$ are as defined above, and Hal represents a halogen atom, e.g. bromo.

The reaction between compounds VII and VIII is conveniently effected at an elevated temperature in a solvent such as N)N-dimethylformamide.

Where $L^1$ in the intermediates of formula V above represents bromo, this compound may be prepared by bromination of the corresponding compound of formula IX:

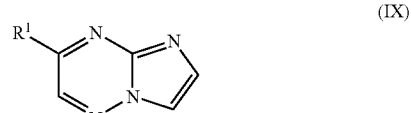

(IX)

wherein $R^1$ is as defined above; typically by treatment with bromine in acetic acid, in the presence of sodium acetate and optionally also potassium bromide.

The intermediates of formula IX may be prepared by reacting bromoacetaldehyde with the requisite compound of formula X:

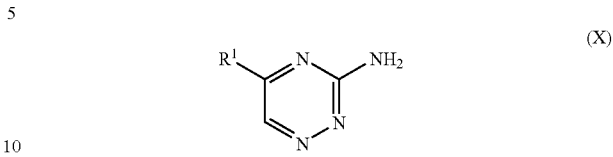

(X)

wherein $R^1$ is as defined above.

The reaction is conveniently carried out by heating the reactants in 1,2-dimethoxyethane, or a lower alkanol such as methanol and/or ethanol, typically at a temperature in the region of 60–80° C.

The intermediates of formula VII above may be prepared from the appropriate compound of formula XI:

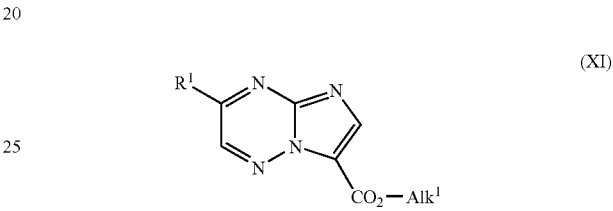

(XI)

wherein $R^1$ is as defined above, and $Alk^1$ represents $C_{1-6}$ alkyl, typically methyl or ethyl; by treatment with ammonia, typically in aqueous ethanol, followed by treatment of the resulting amide derivative with Lawesson's reagent [2,4-bis (4-methoxyphenyl)-1,3-dithia-2,4-diphosphetane-2,4-disulfide], typically in refluxing toluene.

The intermediates of formula XI may be prepared by reacting a compound of formula X as defined above with N,N-dimethylformamide dimethyl acetal, followed by treatment of the product thereby obtained with ethyl bromoacetate.

Both steps of this transformation may conveniently be accomplished by heating under reflux in toluene.

In another procedure, the compounds according to the present invention wherein $R^1$ represents an aryl or heteroaryl moiety may be prepared by a process which comprises reacting a compound of formula XII with a compound of formula XIII:

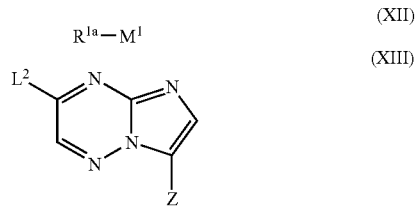

(XII)

(XIII)

wherein Z and $M^1$ are as defined above, $R^{1a}$ represents an aryl or heteroaryl moiety, and $L^2$ represents a suitable leaving group; in the presence of a transition metal catalyst.

The leaving group $L^2$ is typically a halogen atom, e.g. chloro.

The transition metal catalyst of use in the reaction between compounds XII and XIII is suitably tetrakis(triphenylphosphine)-palladium(0), in which case the reaction is conveniently effected at an elevated temperature in a solvent such as N,N-dimethylacetamide, typically in the presence of potassium phosphate or in the presence of lithium chloride and copper(I) iodide. Alternatively, the transition metal catalyst may suitably be tris(dibenzylideneacetone)palladium(0), in which case the reaction is conveniently effected at an elevated temperature in a solvent such as 1,4-dioxane, typically in the presence of tri-tert-butylphosphine and cesium carbonate.

Where $L^2$ in the compounds of formula XIII above represents a halogen atom, these compounds correspond to compounds of formula I as defined above wherein $R^1$ represents halogen, and they may therefore be prepared by any of the methods described above for the preparation of the compounds according to the invention.

In a further procedure, the compounds according to the invention may be prepared by a process which comprises reacting a compound of formula IV as defined above with a compound of formula IX as defined above in the presence of a transition metal catalyst.

The transition metal catalyst of use in the reaction between compounds IV and IX is suitably tetrakis(triphenylphosphine)palladium(0), in which case the reaction is conveniently effected at an elevated temperature in a solvent such as 1,4-dioxane, typically in the presence of cesium carbonate.

Where they are not commercially available, the starting materials of formula IV, VI, VIII, X and XII may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I initially obtained wherein Z is an N-oxypyridinyl moiety may be converted into the corresponding compound wherein Z represents 2-chloropyridinyl by treatment with phosphorus oxychloride. A compound of formula I wherein the moiety Z is substituted by a halogen atom, e.g. chloro or bromo, may be converted into the corresponding compound wherein the moiety Z is substituted by an aryl or heteroaryl group, e.g. 2-cyanophenyl, 2-cyano-4-fluorophenyl, pyridin-3-yl or pyridin-4-yl, by treatment with the requisite aryl or heteroaryl boronic acid or cyclic ester thereof formed with an organic diol, e.g. 2-(4,4,5,5-tetramethyl-[1,3,2]dioxaborolan-2-yl)benzonitrile, 5-fluoro-2-(4,4,5,5-tetramethyl-[1,3,2]dioxaborolan-2-yl)benzonitrile, pyridine-3-boronic acid-1,3-propanediol cyclic ester or pyridine-4-boronic acid, in the presence of a transition metal catalyst such as tetrakis(triphenylphosphine)palladium(0), in which case the reaction is conveniently effected at an elevated temperature in a solvent such as N,N-dimethylacetamide, aqueous 1,2-dimethoxyethane, aqueous 1,4-dioxane or aqueous tetrahydrofuran, typically in the presence of potassium phosphate, sodium carbonate or cesium carbonate; or by treatment with the appropriate stannyl reagent, e.g. 2-tributylstannylbenzonitrile, in the presence of a transition metal catalyst such as dichloro[1,1'-bis(diphenylphosphino)ferrocene]palladium(II), in which case the reaction is conveniently effected at a elevated temperature in a solvent such as N,N-dimethylacetamide, typically in the presence of lithium chloride and copper(I) chloride; or by treatment with the appropriate stannyl reagent in the presence of a transition metal catalyst such as tetrakis(triphenyl-phosphine)palladium(0), in which case the reaction is conveniently accomplished at an elevated temperature in a solvent such as tetrahydrofuran or 1,4-dioxane, typically in the presence of copper(I) iodide; or, where the moiety Z in the desired compound of formula I is substituted by imidazol-1-yl, simply by treatment with imidazole in the presence of a strong base such as lithium hexamethyldisilazide (LiHMDS). A compound of formula I wherein the moiety Z is substituted by pyridinyl may be converted into the corresponding compound wherein Z is substituted by N-oxypyridinyl by treatment with meta-chloroperbenzoic acid. A compound of formula I wherein Z is substituted by a halogen atom, e.g. iodo, may be converted, by treatment with isopropylmagnesium chloride, into a Grignard reagent which may be reacted with an aldehyde such as acetaldehyde to afford a secondary alcohol, e.g. the 1-hydroxyethyl derivative; and this compound may in turn be treated with an oxidising agent, e.g. Dess-Martin periodinane, to afford the corresponding compound of formula I wherein Z is substituted by acetyl. The resulting acetyl derivative may be converted, by treatment with methylmagnesium chloride, into the corresponding compound wherein Z is substituted by 2-hydroxyprop-2-yl; and this compound may in turn be treated with (diethylamino)sulfur trifluoride (DAST) to afford the corresponding compound of formula I wherein Z is substituted by 2-fluoroprop-2-yl. A compound of formula I wherein $R^1$ represents —C(O-Alk$^1$)$_2$R$^a$ initially obtained, wherein Alk$^1$ is as defined above, may be converted into the corresponding compound of formula I wherein $R^1$ represents —COR$^a$ by hydrolysis with a mineral acid, typically aqueous hydrochloric acid. A compound wherein $R^1$ represents formyl may be reduced with sodium triacetoxyborohydride to the corresponding compound wherein $R^1$ represents hydroxymethyl. A compound of formula I wherein $R^1$ represents hydroxymethyl may be oxidised to the corresponding compound of formula I wherein $R^1$ represents formyl by treatment with manganese dioxide. The formyl derivative thereby obtained may be condensed with a hydroxylamine derivative of formula H$_2$N—OR$^b$ to provide a compound of formula I wherein $R^1$ represents —CH=NOR$^b$. Furthermore, a compound of formula I wherein $R^1$ represents —CH=NOH may be treated with triethylamine in the presence of 1,1'-carbonyldiimidazole to afford a corresponding compound of formula I wherein $R^1$ represents cyano. Alternatively, the compound of formula I wherein $R^1$ represents formyl may be reacted with a Grignard reagent of formula R$^a$MgBr to afford a compound of formula I wherein $R^1$ represents —CH(OH)R$^a$, and this compound may in turn be oxidised using manganese dioxide to the corresponding compound of formula I wherein $R^1$ represents —COR$^a$. The latter compound may then be condensed with a hydroxylamine derivative of formula H$_2$N—OR$^b$ to provide a compound of formula I wherein $R^1$ represents —CR$^a$=NOR$^b$. A compound of formula I wherein $R^1$ represents —CH(OH)R$^a$ may be converted into the corresponding compound of formula I wherein $R^1$ represents —CHFR$^a$ by treatment with DAST. Similarly, a compound of formula I wherein $R^1$ represents —COR$^a$ may be converted into the corresponding compound of formula I wherein $R^1$ represents —CF2R$^a$ by treatment with DAST. A compound of formula I wherein $R^1$ represents amino may be converted into the corresponding compound of formula I wherein $R^1$ represents chloro by diazotisation, using sodium nitrite, followed by treatment with copper(I) chloride. A compound of formula I wherein $R^1$ represents —COCH$_s$ may be treated with thioacetamide in the presence of pyridinium tribromide to furnish the corresponding compound of formula I wherein $R^1$ represents 2-methylthiazol-5-yl. Moreover, a compound of formula I wherein $R^1$ is formyl may be treated with (p-tolylsulfonyl)methyl isocyanide (TosMIC) in the presence of potassium carbonate to afford the corresponding compound of formula I wherein $R^1$ represents oxazol-5-yl. A compound of formula I wherein $R^1$ represents hydroxymethyl may be treated with carbon tetrabromide and triphenylphosphine to afford the corresponding compound of formula I wherein $R^1$ represents bromomethyl, which may then be reacted (typically in situ) with the sodium salt of imidazole or 1H-[1,2,4]triazole to provide a compound of formula I wherein $R^1$ represents imidazol-1-ylmethyl or [1,2,4]triazol-1-ylmethyl respectively; or with the sodium salt of 1H-[1,2,3]triazole to provide a mixture of compounds of formula I wherein $R^1$ represents [1,2,3]triazol-1-ylmethyl and [1,2,3]triazol-2-ylmethyl; or with morpholine to provide a compound of formula I wherein $R^1$ represents morpholin-4-ylmethyl.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The following Examples illustrate the preparation of compounds according to the invention.

The compounds in accordance with this invention potently inhibit the binding of [$^3$H-]-flumazenil to the benzodiazepine binding site of human $GABA_A$ receptors containing the α2 and/or α3 and/or α5 subunit stably expressed in Ltk⁻ cells.

Reagents

Phosphate buffered saline (PBS).

Assay buffer: 10 mM $KH_2PO_4$, 100 mM KCl, pH 7.4 at room temperature.

[$^3$]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 and/or α5 subunit of the human $GABA_A$ receptor of 100 nM or less.

EXAMPLE 1

2-[4-(3-Trifluoromethylimidazo[1,2-b][1,2,4]triazin-7-yl)pyridin-2-yl]-benzonitrile a) 3-Amino-5-trifluoromethyl-1,2,4-triazine To a stirred solution of sodium acetate trihydrate (22.62 g, 166.2 mmol) in water (80 ml) was added 1,1-dibromo-3,3,3-trifluoroacetone (21.57 g, 79.9 mmol). The solution was heated at reflux under nitrogen for 30 min, then allowed to cool to room temperature before adding solid aminoguanidine bicarbonate (10.88 g, 79.9 mmol). The resulting pale yellow solution (pH 5) was stirred at room temperature for 3 h, then 4 N aqueous NaOH solution (40 ml, 160 mmol) was added causing a precipitate to appear. The mixture (pH 10) was stirred under nitrogen for a further 39 h. The solid was collected by filtration, washed with water and dried at 60° C. under vacuum to give 6.96 g of a mixture of two isomers in a 28:72 ratio. This was further purified by flash chromatography (silica gel, 30% EtOAc/isohexane), then recrystallised from ethanol to afford 3.53 g (27%) of the title compound: $^1$H NMR (400 MHz, DMSO-$d_6$) δ 8.00 (2H, br s), 9.08 (1H, s).

b) 3-Trifluoromethylimidazo[1,2-b][1,2,4]triazine

A stirred mixture of bromoacetaldehyde diethyl acetal (2.30 ml, 14.8 mmol) in concentrated hydrobromic acid (0.73 ml) and water (0.73 ml) was heated at reflux for 2 h, then poured into ethanol (25 ml). The solution was neutralised to pH 7 with solid sodium hydrogencarbonate, then filtered. To the filtrate was added 3-amino-5-trifluoromethyl-1,2,4-triazine (1.0079 g, 6.14 mmol) and the mixture was stirred at 60° C. for 20 h, then 80° C. for 23 h. The mixture was evaporated in vacuo, and the residue was purified by flash chromatography (silica gel, 35–50% EtOAc/isohexane) to give 0.2593 g (22%) of the title compound: $^1$H NMR (360 MHz, CDCl$_3$) δ 8.20 (1H, d, J 0.8), 8.30 (1H, d, J 0.9), 8.73 (1H, s).

c) 7-Bromo-3-trifluoromethylimidazo[1,2-b][1,2,4]triazine

To a solution of 3-trifluoromethylimidazo[1,2-b][1,2,4]triazine (0.2211 g, 1.18 mmol) in acetic acid (6 ml) was added sodium acetate (0.1470 g, 1.79 mmol), then bromine (90.8 µl, 1.76 mmol). The solution was stirred at room temperature for 6 h, then partitioned between saturated aqueous NaHCO$_3$ (100 ml) and ethyl acetate (100 ml). The aqueous layer (pH 9) was further extracted with ethyl acetate (100 ml), and the combined organic extracts were dried (Na$_2$SO$_4$) and evaporated in vacuo. The residue was purified by flash chromatography (silica gel, 25% EtOAc/isohexane) to afford 0.2073 g (66%) of the title compound: $^1$H NMR (360 MHz, CDCl$_3$) δ 8.30 (1H, s), 8.83 (1H, s).

d) 4-(Tributylstannyl)pyridine 1-oxide

4-Tributylstannylpyridine (3.00 g, 8.15 mmol) and 3-chloroperoxybenzoic acid (2.81 g, 16.3 mmol) in CHCl$_3$ (60 ml) was stirred at 0° C. for 24 h. The mixture was washed with saturated aqueous NaHCO$_3$ (2×200 ml). The organic layer was dried (Na$_2$SO$_4$), filtered, and evaporated in vacuo. Purification by chromatography (silica gel, 0–10% MeOH/EtOAc) gave 2.00 g (64%) of the title compound: $^1$H NMR (360 MHz, CDCl$_3$) δ 0.80–1.60 (27H, m), 7.42 (2H, d, J 5.0), 8.35 (2H, d, J 5.0).

e) 7-(1-Oxypyridin-4-yl)-3-trifluoromethylimidazo[1,2-b][1,2,4]triazine

A mixture of 7-bromo-3-trifluoromethylimidazo[1,2-b][1,2,4]triazine (0.50 g, 1.87 mmol), 4-(tributylstannyl)pyridine 1-oxide (1.07 g, 2.81 mmol), and copper(I) iodide (0.04 g, 0.19 mmol) in N,N-dimethylacetamide (30 ml) was degassed before adding tetrakis(triphenylphosphine)-palladium(0) (0.11 g, 0.09 mmol), degassing again and then heating at 100° C. for 17 h. The mixture was allowed to cool to an ambient temperature, filtered, then partitioned between aqueous NaCl (200 ml) and EtOAc (200 ml). The organic layer was dried (Na$_2$SO$_4$), filtered and evaporated in vacuo. Purification by chromatography (silica gel, 5% MeOH/CH$_2$Cl$_2$) gave 370 mg (70%) of the title compound: $^1$H NMR (360 MHz, CDCl$_3$) δ 8.13 (2H, d, J 7.4), 8.35 (2H, d, J 7.4), 8.70 (1H, s), 8.87 (1H, s).

f) 7-(2-Chloropyridin-4-yl)-3-trifluoromethylimidazo[1,2-b][1,2,4]triazine 7-(1-Oxypyridin-4-yl)-3-trifluoromethylimidazo[1,2-b][1,2,4]triazine (0.04 g, 0.142 mmol) in phosphorus oxychloride (1.5 ml) was stirred at 100° C. for 18 h. The mixture was evaporated in vacuo then neutralised with NaHCO$_3$. The aqueous layer was extracted with Et$_2$O, dried (Na$_2$SO$_4$) and evaporated in vacuo: $^1$H NMR (400 MHz, CDCl$_3$) δ 7.96 (1H, dd, J 1.6, 5.1), 8.17 (1H, dd, J 0.8, 0.8), 8.58 (1H, d, J 5.5), 8.76 (1H, s), 8.92 (1H, s).

g) 2-[4-(3-Trifluoromethylimidazo[1,2-b][1,2,4]triazin-7-yl)pyridin-2-yl]-benzonitril A mixture of 2-bromobenzonitrile (20 g, 110 mmol), bis(pinacolato)diboron (30.4 g, 120 mmol) and potassium acetate (32.4 g, 330 mmol) in 1,4-dioxane (100 ml) and dimethylsulfoxide (20 ml) was degassed with nitrogen for 30 min. Dichloro[1,1'-bis(diphenylphosphino)ferrocene]palladium(II) dichloromethane adduct (2.00 g, 2.73 mmol) was added and the mixture heated at 90° C. for 18 h. The mixture was cooled to ambient temperature and partitioned between diethyl ether and 2 N sodium hydroxide solution. The organic layer was discarded and the aqueous phase cooled to 0° C. and adjusted to pH 7 by the addition of 36% hydrochloric acid. The solid was collected by filtration, washed with water and left to air dry to give 19 g (76%) of 2-(4,4,5,5-tetramethyl-[1,3,2]dioxaborolan-2-yl)benzonitrile as an off-white solid: $^1$H NMR (360 MHz, CDCl$_3$) δ 1.39 (12H, s), 7.52 (1H, td, J 7.7, 1.4), 7.57 (1H, td, J 7.7, 1.4), 7.69 (1H, dd, 7.7, 1.4), 7.89 (1H, dd, J 7.4, 1.1).

7-(2-Chloropyridin-4-yl)-3-trifluoromethylimidazo[1,2-b][1,2,4]triazine was coupled with 2-(4,4,5,5-tetramethyl-[1,3,2]dioxaborolan-2-yl)benzonitrile in the presence of tetrakis(triphenylphosphine)palladium(0) and sodium carbonate, at 80° C. in aqueous 1,2-dimethoxyethane, to give the title compound in 4% yield: $^1$H NMR (360 MHz, CDCl$_3$) δ 7.60 (1H, td, J 1.1, 7.7), 7.78 (1H, td, J 1.1, 7.7), 7.89 (1H, dd, J 1.1, 7.7), 7.97 (1H, dd, J 7.0, 0.7), 8.13 (1H, dd, J 1.8, 5.3), 8.65 (1H, d, J 0.7), 8.84 (1H, s), 8.94 (1H, s), 8.99 (1H, dd, J 0.7, 5.3).

EXAMPLE 2

5-Fluoro-2-[4-(3-trifluoromethylimidazo[1,2-b][1,2,4]triazin-7-yl)pyridin-2-yl]benzonitrile 2-Bromo-5-fluorobenzonitrile was converted to 5-fluoro-2-(4,4,5,5-tetramethyl-[1,3,2]dioxaborolan-2-yl)benzonitrile as described in Example 1, step g, to give a straw-coloured solid: $^1$H NMR (360 MHz, CDCl$_3$) δ 1.38 (12H, s), 7.27 (1H, ddd, J 8, 8, 2), 7.39 (1H, dd, J 9, 2), 7.90 (1H, dd, J 8, 6).

7-(2-Chloropyridin-4-yl)-3-trifluoromethylimidazo[1,2-b][1,2,4]triazine was reacted with 5-fluoro-2-(4,4,5,5-tetramethyl-[1,3,2]dioxaborolan-2-yl)benzonitrile by a similar procedure to that described in Example 1, step g, to give the title compound in 24% yield: $^1$H NMR (400 MHz, CDCl$_3$) δ 7.48 (1H, ddd, J 2.7, 7.8, 8.6), 7.57 (1H, dd, J 2.7, 8.2), 8.01 (1H, dd, J 5.3, 8.8), 8.08 (1H, dd, J 1.8, 5.3), 8.63 (1H, dd, J 1.0, 1.8), 8.82 (1H, s), 8.92 (1H, s), 8.95 (1H, dd, J 1.0, 5.3).

EXAMPLE 3

4-(3-Trifluoromethylimidazo[1,2-b][1,2,4]triazin-7-yl)-[2,4']bipyridinyl

A mixture of 7-(2-chloropyridin-4-yl)-3-trifluoromethylimidazo[1,2-b][1,2,4]triazine (0.10 g, 0.33 mmol) (prepared as described in Example 1), pyridine-4-boronic acid (50 mg, 0.40 mmol) and sodium carbonate (600 µl of a 2 M solution) in 1,4-dioxane (3 ml) was degassed by bubbling nitrogen through for 20 min. Tetrakis(triphenylphosphine) palladium(0) (50 mg, 0.04 mmol) was added and the mixture heated at 90° C. for 4 h. Solvent was removed in vacuo from the mixture and the residue partitioned between dichloromethane (50 ml) and water (30 ml). The organic layer was washed with saturated brine then dried (MgSO$_4$), filtered and evaporated in vacuo. Purification by chromatography (silica gel, 5% MeOH/CH$_2$Cl$_2$) gave 28 mg of the title compound as a yellow solid: $^1$H NMR (400 MHz, CDCl$_3$)

δ 7.98–7.99 (2H, m), 8.06 (1H, dd, J 1.6, 5.1), 8.59 (1H, s), 8.79–8.84 (3H, m), 8.94 (1H, dd, J 0.8, 4.3), 8.95 (1H, s); MS (ES$^+$) m/z 343 [M+H]$^+$.

EXAMPLE 4

5-[3-(1-Hydroxy-1-methylethyl)imidazo[1,2-b][1,2,4]triazin-7-yl]-2-oxo-2H 1,2']bipyridinyl-3'-carbonitrile a) 1,1-Dibromo-3-hydroxy-3-methylbutan-2-one To a stirred solution of 3-methyl-3-hydroxy-2-butanone (40 g, 0.392 mol) in anhydrous dichloromethane (2.2 l) under nitrogen was added solid pyridinium tribromide (250.4 g, 0.784 mol) in portions and the mixture was stirred at room temperature for 14 h. The mixture was then washed with dilute aqueous sodium hydrogensulphite (500 ml), then saturated aqueous NaCl (500 ml), dried (Na$_2$SO$_4$), and evaporated in vacuo. The residue was purified by flash chromatography (silica gel, CH$_2$Cl$_2$) to afford 31.4 g (31%) of the title compound as a colourless oil: $^1$H NMR (360 MHz, CDCl$_3$) δ 1.54 (6H, s), 2.45 (1H, br s), 6.62 (1H, s).

b) 2-(3-Amino-[1,2,4]triazin-5-yl)propan-2-ol and 2-(3-Amino-[1,2,4]triazin-6-yl)propan-2-ol To a stirred solution of sodium acetate trihydrate (32.9 g, 0.342 mol) in water (90 ml) was added 1,1-dibromo-3-hydroxy-3-methylbutan-2-one (29.6 g, 0.114 mol). The solution was heated at reflux under nitrogen for 30 min, then allowed to cool to room temperature before adding solid aminoguanidine bicarbonate (15.54 g, 0.114 mol). The resulting pale yellow solution (pH 5) was stirred at room temperature for 15 min, then 4 N aqueous NaOH solution (56.9 ml, 0.228 mol) was added and the mixture (pH 10) was stirred under nitrogen for a further 14 h. The solution was continuously extracted with warm dichloromethane over a period of 24 h. After this time the solvent was evaporated to leave a residue which was triturated with diethyl ether to give a solid. The solid was collected by filtration and dried at 60° C. under vacuum to give 8.17 g (47%) of a mixture of two isomers in a 60:40 ratio with the required 2-(3-amino-[1,2,4]triazin-5-yl)propan-2-ol being the major product: $^1$H NMR (360 MHz, DMSO-d$_6$) δ 1.38 (major) and 1.47 (minor) (6H, s), 5.30 (major) and 5.43 (minor) (1H, br s), 7.01 (major) and 7.06 (minor) (2H, br s), 8.43 (major) and 8.80 (minor) (1H, s); MS (ES$^+$) m/z 155 [M+H]$^+$.

c) 2-(Imidazo[1,2-b][1,2,4]triazin-3-yl)propan-2-ol

A stirred mixture of bromoacetaldehyde diethyl acetal (16.5 ml, 0.106 mol) in concentrated hydrobromic acid (4.13 ml) and water (4.13 ml) was heated at reflux for 40 min, then poured into ethanol (175 ml). The solution was neutralised to pH 7 with solid sodium hydrogencarbonate, then filtered, washing the solid with more ethanol (30 ml). To the filtrate was added a 60:40 mixture of 2-(3-amino-[1,2,4]triazin-5-yl)propan-2-ol and 2-(3-amino-[1,2,4]triazin-6-yl)propan-2-ol (8.17 g, 0.053 mol) and the mixture was stirred at reflux temperature for 6 h. The mixture was evaporated in vacuo, and the residue was triturated with hot dichloromethane and filtered. The solid was triturated with hot acetone and collected by filtration again to leave a white solid (14 g). The solid was dissolved in water (30 ml) and continuously extracted with hot dichloromethane over a period of 24 h. The organic layer was separated and concentrated under vacuum to leave a thick yellow oil (3 g) which favoured the required isomer in a ratio of 4:1. The required product was obtained in pure form by flash chromatography (silica gel, 2% MeOH/CH$_2$Cl$_2$) to give 2.12 g (23%) of the title compound as a pale yellow solid: $^1$H NMR (360 MHz, CDCl$_3$) δ 1.69 (6H, s), 3.69 (1H, br s), 7.93 (2H, s), 8.70 (1H, s).

d) 2-(7-Bromoimidazo[1,2-b][1,2,4]triazin-3-yl)propan-2-ol

To a stirred solution of 2-(imidazo[1,2-b][1,2,4]triazin-3-yl)propan-2-ol (5.55 g, 31.1 mmol) in acetic acid (100 ml) was added sodium acetate (3.83 g, 46.7 mmol), then, dropwise over 5 min, a solution of bromine (1.77 ml, 34.4 mmol) in acetic acid (12 ml). The solution was stirred at room temperature for 25 min, then partitioned between saturated aqueous NaHCO$_3$ (2 l) and ethyl acetate (1 l). The aqueous layer (pH 7) was further extracted with ethyl acetate (1 l), and the combined organic extracts were dried (Na$_2$SO$_4$) and evaporated iii, vacuo. The residue was purified by flash chromatography (silica gel, 2% MeOH/CH$_2$Cl$_2$) to afford 6.17 g (77%) of the title compound as a yellow solid: $^1$H NMR (360 MHz, CDCl$_3$) δ 1.70 (6H, s), 3.12 (1H, br s), 7.95 (1H, s), 8.80 (1H, s).

e) 5-Bromo-2-oxo-2H-[1,2']bipyridinyl-3'-carbonitrile

To 5-bromo-2-pyridone (1.0 g) and 2-chloro-3-cyanopyridine (1.0 g) in dry N,N-dimethylformamide (20 ml) was added caesium carbonate (2.73 g), and the mixture heated at 75° C. under a nitrogen atmosphere for 24 h. The solvent was removed in vacuo from the mixture and the residue partitioned between ethyl acetate and water. The organic layer was evaporated and the residue purified by chromatography (silica gel, 0 to 4% MeOH/CH$_2$Cl$_2$) to give the title compound, crystallised from diethyl ether/isohexane: $^1$H NMR (400 MHz, CDCl$_3$) δ 8.81 (1H, dd, J 2.0, 5.1), 8.17 (1H, dd, J 1.8, 7.6), 7.67 (1H, d, J 2.7), 7.56 (1H, dd, J 4.9, 7.6), 7.49 (1H, dd, J 2.5, 10.0), 6.62 (1H, d, J 9.8); MS (ES$^+$) m/z 276 and 278 [M+H]$^+$.

f) 5-(5,5-Dimethyl-[1,3,2]dioxaborinan-2-yl)-2-oxo-2H-[1,2']bipyridinyl-3'-carbonitrile To a degassed mixture of 5-bromo-2-oxo-2H-[1,2']bipyridinyl-3'-carbonitrile (0.281 g), bis(neopentyl glycolato)diboron (0.275 g), dry 1,4-dioxane (5 ml) and potassium acetate (0.212 g), under an atmosphere of dry nitrogen, was added [1,1'-bis(diphenylphosphino)ferrocene]-dichloropalladium(II) dichloromethane complex (0.03 g). The degassed mixture was heated at 80° C. under a nitrogen atmosphere for 24 h. After cooling to 25° C., 1 M aqueous sodium hydroxide (24 ml) was added and the mixture stirred vigorously for 0.5 h in air. The mixture was filtered, and the filtrate acidified to pH 4 by addition of 2 N aqueous hydrochloric acid (12 ml). The product was extracted with dichloromethane, and the solvent stripped at reduced pressure to afford a brown oil, used without further purification. MS (ES$^+$) m/z 242 (boronic acid) and 310 (boronate ester) [M+H]$^+$.

g) 5-[3-(1-Hydroxy-1-methylethyl)imidazo[1,2-b][1,2,4]triazin-7-yl]-2-oxo-2H-[1,2']bipyridinyl-3'-carbonitrile To a degassed mixture of 5-(5,5-dimethyl-[1,3,2]dioxaborinan-2-yl)-2-oxo-2H-[1,2']bipyridinyl-3'-cabonitrile (from step f), 2-(7-bromo-imidazo[1,2-b][1,2,4]triazin-3-yl)propan-2-ol (from step d) (0.23 g), dry 1,4-dioxane (5 ml), and 2 M aqueous sodium carbonate (3 ml), was added tetrakis(triphenylphosphine)palladium(0) (0.12 g). The mixture was heated at 95° C. under a nitrogen atmosphere for 24 h. After cooling to 25° C., the reaction was diluted with ethyl acetate, and the organic phase separated. The solvent was evaporated at reduced pressure and the residue purified by chromatography (silica gel, 5% MeOH/CH$_2$Cl$_2$) to give the title compound, crystallised from hot isopropanol as a yellow solid: 1H NMR (400 MHz, DMSO-$d_6$) δ 8.98 (1H, s), 8.97 (1H, d, J 2.0), 8.62–8.68 (2H, m), 8.40 (1H, s), 8.32 (1H, dd, J 2.7, 9.8), 7.85 (1H, dd, J 5.1, 7.8), 6.83 (1H, d, J 9.8), 5.75 (1H, s), 1.54 (6H, s); MS (ES$^+$) m/z 374 [M+H]$^+$.

The invention claimed is:

1. A compound of formula I, or a pharmaceutically acceptable salt thereof:

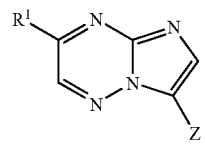

(I)

wherein:

Z represents a five-membered heteroaromatic ring selected from furan, thiophene, pyrrole, oxazole, thiazole, isoxazole, isothiazole, imidazole, pyrazole, oxadiazole, thiadiazole, triazole and tetrazole, which is unsubstituted or substituted; or Z represents a six-membered heteroaromatic ring selected from pyridine, pyrazine, pyrimidine and pyridazine, which is unsubstituted or substituted;

$R^1$ represents hydrogen, hydrocarbon, a heterocyclic group, halogen, cyano, trifluoromethyl, nitro, —OR$^a$, —SR$^a$, —SOR$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$ or —CR$^a$=NOR$^b$; and $R^a$ and $R^b$ independently represent hydrogen, hydrocarbon or a heterocyclic group.

2. The compound of claim 1 of the formula IA, or a pharmaceutically acceptable salt thereof:

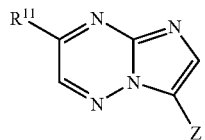

(IA)

wherein:

$R^{11}$ represents hydrogen, C$_{1-6}$ alkyl, cyano(C$_{1-6}$)alkyl, halo(C$_{1-6}$)alkyl, dihalo(C$_{1-6}$)alkyl, hydroxy(C$_{1-6}$)alkyl, C$_{1-6}$ alkoxy(C$_{1-6}$)alkyl, di(C$_{1-6}$)alkoxy(C$_{1-6}$)alkyl, C$_{3-7}$ cycloalkyl, heteroaryl, C$_{1-6}$ alkyl-heteroaryl, heteroaryl(C$_{1-6}$)alkyl, halogen, cyano, trifluoromethyl, C$_{1-6}$ alkoxy, formyl, C$_{2-6}$ alkylcarbonyl, C$_{2-6}$ alkoxycarbonyl or -CR$^4$=NOR$^5$;

$R^4$ represents hydrogen or C$_{1-6}$ alkyl; and $R^5$ represents hydrogen, C$_{1-6}$ alkyl, hydroxy(C$_{1-6}$)alkyl or di(C$_{1-6}$)alkylamino(C$_{1-6}$)alkyl.

3. The compound of claim 2 of the formula IIA, or a pharmaceutically acceptable salt thereof:

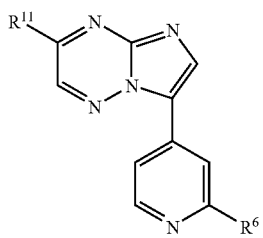

(IIA)

wherein:

$R^6$ represents hydrogen, halogen, cyano, trifluoromethyl, C$_{1-6}$ alkyl, halo(C$_{1-6}$)alkyl, dihalo(C$_{1-6}$)alkyl, hydroxy(C$_{1-6}$)alkyl, C$_{1-6}$ alkoxy(C$_{1-6}$)alkyl, C$_{3-7}$ cycloalkyl, C$_{3-7}$ heterocycloalkyl, benzyl-tetrahydropyridinyl, C$_{1-6}$ alkoxy, methyltriazolyl(C$_{1-6}$)alkoxy, C$_{1-6}$ alkylthio, C$_{1-6}$ alkylsulphonyl, C$_{2-6}$ alkylcarbonyl, amino, C$_{1-6}$ alkylamino, di(C$_{1-6}$)alkylamino, C$_{2-6}$ alkylcarbonylamino, phenyl, (C$_{1-6}$)alkyl-phenyl, halophenyl, dihalophenyl, trihalophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (halo)(trifluoromethyl)phenyl, nitrophenyl, methoxyphenyl, (halo)(methoxy)phenyl, trifluoromethoxy-phenyl, (halo)(trifluoromethoxy)phenyl, methylenedioxy-phenyl, (C$_{2-6}$) alkylcarbonyl-phenyl, trifluorothio-phenyl, (C$_{1-6}$) alkylsulphonyl-phenyl, di (C$_{1-6}$)alkylaminocarbonyl-phenyl, di(C$_{1-6}$)alkylaminosulphonyl-phenyl, (halo)(morpholinylmethyl)phenyl, (halo)(pyridinyl)phenyl, imidazolyl-phenyl, thiadiazolyl-phenyl, methylthiadiazolyl-phenyl, (halo)(triazolyl)phenyl, methyltetrazolyl-phenyl or optionally substituted heteroaryl, the optional substituents on the heteroaryl moiety being selected from oxy, halogen, cyano and C$_{1-6}$ alkyl.

4. The compound of claim 3 of the formula IIB, or a pharmaceutically acceptable salt thereof:

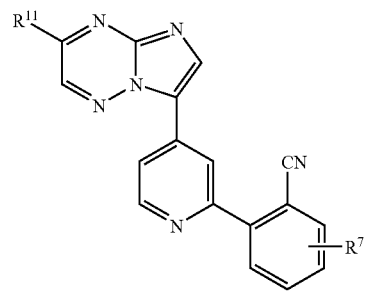

(IIB)

wherein:

$R^7$ represents hydrogen or fluoro.

5. The compound of claim 2 of the formula IIC, or a pharmaceutically acceptable salt thereof:

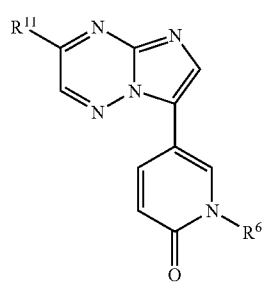

(IIC)

wherein:

$R^6$ represents hydrogen, halogen, cyano, trifluoromethyl, C$_{1-6}$ alkyl, halo(C$_{1-6}$)alkyl, dihalo(C$_{1-6}$)alkyl, hydroxy(C$_{1-6}$)alkyl, C$_{1-6}$ alkoxy(C$_{1-6}$)alkyl, C$_{3-7}$ cycloalkyl, C$_{3-7}$ heterocycloalkyl, benzyl-tetrahydropyridinyl, C$_{1-6}$ alkoxy, methyltriazolyl(C$_{1-6}$)alkoxy, C$_{1-6}$ alkylthio, $C_{1-6}$ alkylsulphonyl, $C_{2-6}$ alkylcarbonyl, amino, $C_{1-6}$alkylamino, di($C_{1-6}$)alkylamino, $C_{2-6}$ alkylcarbonylamino, phenyl, ($C_{1-6}$)alkyl-phenyl, halophenyl, dihalophenyl, trihalophenyl, (fluoro)(methyl)phenyl, cyanophenyl, (cyano)(fluoro)phenyl, (cyano)(difluoro) phenyl, difluoromethyl-phenyl, trifluoromethyl-phenyl, (methyl)(trifluoromethyl)phenyl, (halo)(trifluoromethyl)phenyl, nitrophenyl, methoxyphenyl, (halo)(methoxy)phenyl, trifluoromethoxy-phenyl, (halo)(trifluoromethoxy)phenyl, methylenedioxy-phenyl, ($C_{2-6}$) alkylcarbonyl-phenyl, trifluorothio-phenyl, ($C_{1-6}$) alkylsulphonyl-phenyl, di($C_{1-6}$)alkylaminocarbonyl-phenyl, di($C_{1-6}$)alkylaminosulphonyl-phenyl, (halo)(morpholinylmethyl)phenyl, (halo)(pyridinyl)phenyl, imidazolyl-phenyl, thiadiazolyl-phenyl, methyithiadiazolyl-phenyl, (halo)(triazolyl)phenyl, methyltetrazolyl-phenyl or optionally substituted heteroaryl, the optional substituents on the heteroaryl moiety being selected from oxy, halogen, cyano and $C_{1-6}$ alkyl.

6. A compound which is selected from:

2-[4-(3-trifluoromethylimidazo[1,2-b][1,2,4]triazin-7-yl) pyridin-2-yl]-benzonitrile;

5-fluoro-2-[4-(3-trifluoromethylimidazo[1,2-b][1,2,4]triazin-7-yl)pyridin-2-yl] benzonitrile;

4-(3-trifluoromethylimidazo[1,2-b][1,2,4]triazin-7-yl)-[2,4']bipyridinyl;

5-[3-(1-hydroxy-1-methylethyl)imidazo[1,2-b][1,2,4]triazin-7-yl]-2-oxo-2H-[1,2]bipyridinyl-3'-carbonitrile;

and pharmaceutically acceptable salts thereof.

7. A pharmaceutical composition comprising a compound of claim 1 or a pharmaceutical acceptable salt thereof and a pharmaceutically acceptable carrier.

* * * * *